United States Patent [19]

Stephen et al.

[11] Patent Number: 5,232,441
[45] Date of Patent: Aug. 3, 1993

[54] METHOD OF TREATING SCHISTOSOMAL INFESTATIONS BY IONTOPHORESIS

[75] Inventors: Robert L. Stephen, Salt Lake City, Utah; Franco Lugnani, Trieste, Italy; Cino Rossi, Rome, Italy; Silvio Eruzzi, Mantova, Italy

[73] Assignee: Physion S.r.L., Mirandola, Italy

[21] Appl. No.: 885,942

[22] Filed: May 18, 1992

[51] Int. Cl.⁵ .............................................. A61M 31/00
[52] U.S. Cl. ........................................ 604/49; 604/20; 604/21; 128/898
[58] Field of Search ................... 604/20, 49; 128/898, 128/798, 802, 803

[56] References Cited

U.S. PATENT DOCUMENTS

| 4,158,049 | 6/1979 | Pelley et al. | 424/1 |
| 4,411,648 | 10/1983 | Davis et al. | 604/21 |
| 4,874,850 | 10/1989 | Paradies | 546/321 |

Primary Examiner—Stephen C. Pellegrino
Assistant Examiner—Michael Rafa
Attorney, Agent, or Firm—Jacobson & Johnson

[57] ABSTRACT

A method of treating schistosomal infestations by both adult worms and eggs-miracidia, residing in the veins, venules and nearby tissues either of the bladder and ureters or of the colorectal regions of the intestines, including the locally administration by iontophoresis of at least an antischistosomal drug in the form of a solution.

21 Claims, 1 Drawing Sheet

METHOD OF TREATING SCHISTOSOMAL INFESTATIONS BY IONTOPHORESIS

BACKGROUND OF THE INVENTION

This invention relates to a method of treating schistosomal infestations by both adult worms and eggs-miracidia, particularly residing in the veins, venules and nearby tissues either of the bladder and ureters, or of the colo-rectal regions of the intestines, by iontophoresis.

Known in the art is the systemic chemotherapy of schistosomiasis by intravenous or intramuscular administration of antischistosomal drugs such as trivalent or pentavalent antimony compounds or, more recently, by oral administration of antischistosomal drugs such as niridazole, metrifonate, oxamniquine and praziquantel.

Illustrative examples of trivalent antimony compounds used in the treatment of schistosomiasis are salts with organic acids such as: antimony potassium or sodium tartrate, sodium antimonyl gluconate, antimony sodium thioglycollate, antimony thioglycollamide, sodium antimony dimercaptosuccinate, stibophen, i.e. pentasodium antimony bis(catechol-3,5-disulphonate) heptahydrate.

The pentavalent antimony compounds are typified by sodium stibogluconate even if other salts thereof with organic acids can be used. The antimony compounds are slowly, irregularly and only partially absorbed from the intestinal tract and are therefore administered by injection. They are known for their toxic effects. The toxicity of antimony, closely resembling that of arsenic, may manifest as intestinal irritation, chemical pneumonia, cardiac dysfunction, liver damage, joint and muscle pain and vascular collapse.

The advent of more easily administered, effective and generally less toxic antischistosomal drugs, has resulted in the virtual abandonment of the trivalent antimony compounds.

Niridazole was the first of the effective orally-administered antischistosomal drugs but it has some marked toxic effects as hallucinations, convulsions, liver damage, destruction of erythrocyte and changes in the electrocardiogram. It has one side effect which makes it pertinent for the object of the present invention, namely a strong anti-inflammatory action.

Metrifonate is another effective orally-administered antischistosomal drug, an organophosphate especially effective in the treatment of infections caused by *S. mansoni* and *S. hematobium* resulting in a 90% reduction in egg counts and a 40–90% cure rate. Side effects appears when the patient comes into contact with other organophosphates, such insecticides and there are cumulative and occasionally disastrous episodes of poisoning.

Another orally administered antischistosomal drug is oxamniquine. This drug is effective only in the treatment of *S. mansoni* infections and displays a blatant sexual discrimination, only male worms being affected. The treatment results in a 90–95% reduction in egg counts and a cure rate of 70–100%.

The most valuable of the presently known antischistosomal drugs seems to be praziquantel. It is effective against all five schistosomal species and results in a 95% reduction in egg counts and 85% cure rate.

Systemic chemotherapy of schistosomiasis although very successful in reducing the intensity of infestations, results in a failure rate of 5–60% (depending upon the source of reports) in terms of actually curing (obliterating) the disease.

Even with the recent, orally administered antischistosomal drugs effecting dramatic reductions in the infestations, treated individuals although often well in themselves, are still spreading infection from residual adult worms laying eggs which are transmitted via the bladders or intestine to outside bodies of water, allowing the propagation of schistosomal infestations.

SUMMARY OF THE INVENTION

A main object of the present invention is that of providing a method of treating schistosomal infestations by both adult worms and eggs-miracidia, which assists in full eradication of infestations and reduces the incidence and severity of secondary tissue scarring.

Other object of the present invention is that of providing a method of treating schistosomal infestations providing high localized concentrations of antischistosomal drugs, advantageously also in conjunction with anti-inflammatory drugs, within the tissues of the bladder and lower ureteric walls and within the tissues of the colorectal walls.

These and other objects, which will appear more clearly from the following disclosure, are achieved by a method of treating schistosomal infestations by both adult worms and eggs-miracidia, localized in the veins, venules and nearby tissues either of the bladder and ureters or of the colorectal regions of the intestine which comprises administering locally by iontophoresis at least an antischistosomal drug in the form of a solution.

According to the method of the present invention one or two, or even more, antischistosomal drugs can be administered. Furthermore the antischistosomal drug(s) can also be administered in conjunction with other drugs, for example anti-inflammatory drugs of known type. When using more than one antischistosomal drug, their total concentration should guarantee the requested dosage for an effective antischistosomal treatment, according to the known dosages in the field. When using also other drugs, such as anti-inflammatory drugs, they have to be used in a concentration giving the effective dosages commonly used in the field for the specific anti-inflammatory drug used.

When the drugs employed are ionizable compounds they can be used either alone or in any of the above mentioned combinations with other drugs.

When the drugs are instead compounds which can only difficultly be ionized, or can not be ionized, then their administration through the method of the present invention should rely on phenomena of electrophoresis accompanying ion migration through iontophoresis.

Therefore, for such difficultly ionizable drugs, a preferred embodiment comprises administering them in conjunction with another drug which is easily ionizable.

Preferred antischistosomal drugs, usable in the iontophoretic method according to the present invention are selected from the group consisting of a trivalent antimony compound, a pentavalent antimony compound, niridazole, metrifonate, oxamniquine, praziquantel, mixture thereof and salts thereof.

As anti-inflammatory drugs ionizable esterified corticosteroids are preferably used, for example dexamethasone phosphate.

Advantageously, drug(s) are locally administered by iontophoresis/electrophoresis, as pure aqueous solution(s) with any physiological buffer/electrolyte, said drug(s) being preferably selected from niridazole, metrifonate, oxamniquine, praziquantel and esterified corticostereoids.

The present invention is based on the finding that the techniques of iontophoresis provide methods of achieving high local concentrations of antischistosomal agents to the venous sites containing adult worms and also to the surrounding tissues wherein lie the entrapped eggs.

Essentially, this invention will achieve high localized concentrations of antischistosomal and anti-inflammatory drugs within the tissues of the bladder and lower ureteric walls and within the tissues of the colo-rectal walls by means of iontophoresis.

The application of an electric field to a solution of drugs contained within the colo-rectal region of the intestine will ensure that the rate of drug delivery into surrounding tissues is accelerated and it becomes more controllable simply by varying the strength of the electric field (the current) and/or the time of application of the electric field. Furthermore, the application of an electric field following to instillation of a drug solution into the bladder, will ensure delivery of drugs into and across intact urothelium and thus great acceleration of administration of drugs into the bladder wall as compared to rates achieved by passive diffusion; and fine control by manipulation of applied current and time of application of the current.

The method of the present invention is carried out by means of any iontophoretic device suitable for intracorporeal application.

Illustratively, the method of the present invention comprises:

a) inserting a catheter via the urethra into the bladder or via rectum within a selected segment of the colo-rectal region, said catheter encompassing an active electrode of appropriate polarity connected to an external power source;

b) infusing via said catheter a volume of drug(s) ranging from 20 to 500 ml (of the patient's weight), as a solution at a concentration from 0.2% to 10% w/v, having ionization characteristics suitable either for iontophoretic administration or for electrophoretic administration in conjunction with iontophoretic delivery of ionized species;

c) placing in contact with a suitable skin location, an indifferent electrode of opposite polarity to said active electrode;

d) supplying an electrical current from said external power source with matching polarities to said active electrode and said indifferent electrode thereby permitting passage of current and consequent administration of said drug(s) into the tissues surrounding the active electrode.

Intravesical (into the bladder) instillation of drug solutions is easily achieved by insertion into the bladder of a catheter with or without a single anchoring balloon, drainage of bladder contents (urine) and infusion of solutions via the catheter. This catheter may contain a conductive element intrinsic within or upon its wall or an active electrode is inserted down the lumen of catheter as described in pending U.S. patent application Ser. No. 07/765.139.

BRIEF DESCRIPTION OF THE DRAWING

Further characteristics and advantages of the invention will become apparent from the description of a preferred but not exclusive embodiment of the device according to the invention, illustrated only by way of a non-limitative example in the accompanying drawing, wherein.

DESCRIPTION OF THE PREFERRED EMBODIMENT

Figure 1:
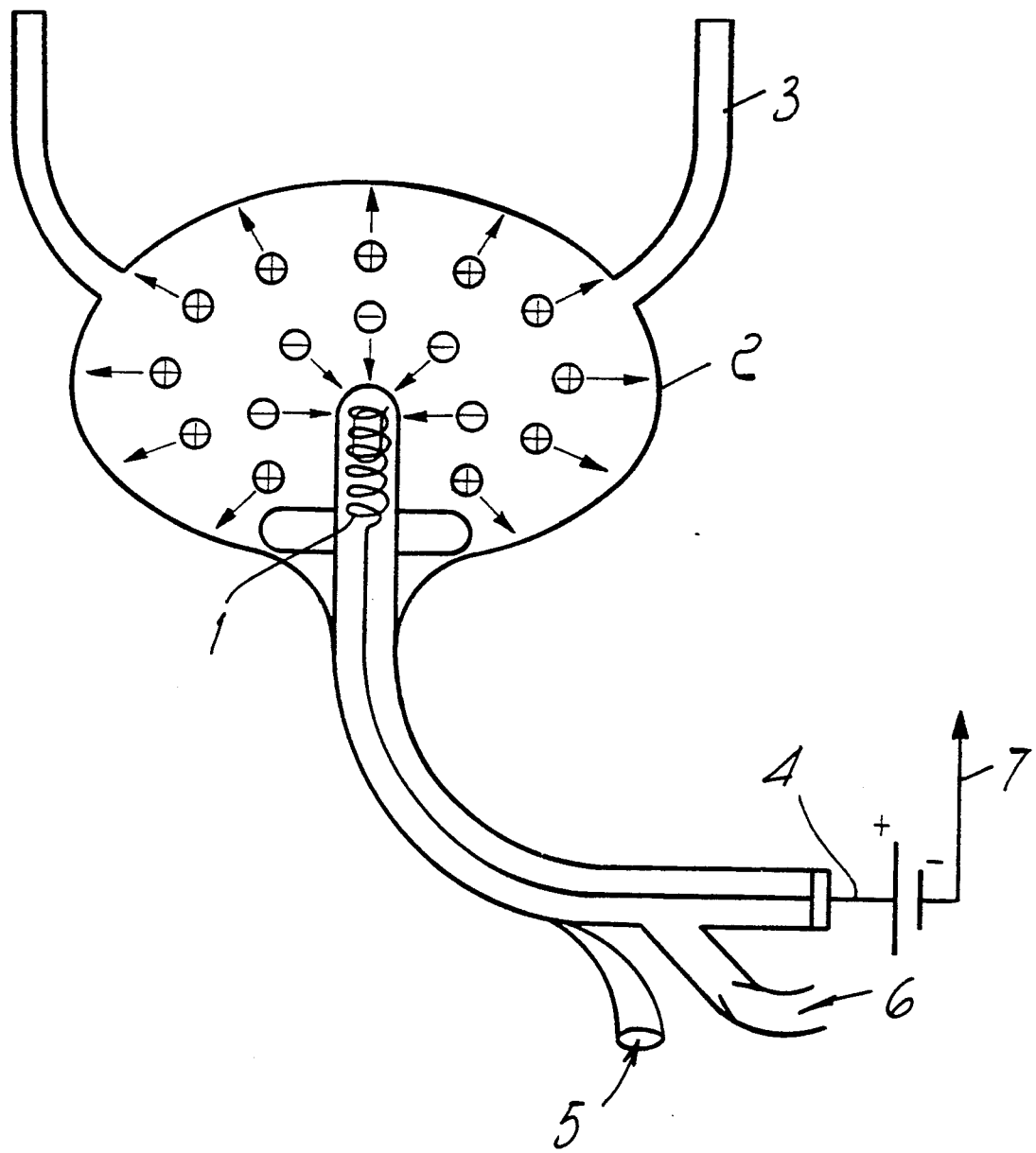
FIG. 1 is a schematic view of a iontophoresis device, according to the invention with a spiral electrode inserted in the bladder.

With reference to the above figure, the iontophoresis device according to the invention, comprises a spiral electrode (1) positively charged to repel the ions of the same polarity.

Obviously, more than one conduct may be provided, for example, one conduit for feeding the drugs in solution (6) and at least one other conduit (5) for feeding other substances to the spiral electrode (1).

The spiral electrode (1) is connected by means of a conductive wire (4) to an external DC power source of positive polarity to the drugs in the solution (6) and a second dispersive electrode (7) runs from the power source to a convenient area of the skin, usually the thigh or the abdominal wall.

Although the DC mode, whether constant or pulsed, is usual for iontophoresis/electrophoresis, a biased AC mode is sometimes advantageous and may also be employed.

Administration of drugs into colo-rectal walls is similar. In order to achieve consistent rates of drug delivery, treatments should be preceded by colo-rectal lavage in order to remove fecal contents. Then a catheter is inserted rectally and positioned so that a segment of the catheter containing apertures lies within the region designated for the treatment and two balloons on the catheter are inflated to isolate this designated section of intestine. The electrodes, connections to the power source and the characteristics of the electrical current are the same as those used with the intravesical catheter.

It has been found that the method according to the present invention allows to achieve markedly increased quantities and concentrations of antischistosomal and anti-inflammatory drugs to the tissues and venous drainage of the bladder-lower ureters and colo-rectal intestine as compared with the only marginal amounts of these same drugs administered systemically.

To illustrate the method of this invention, data referring to the systemically and iontophoretic administration of trivalent antimony compounds, pentavalent antimony compounds, niridazole, metrifonate, oxamniquine, corticosteroid drugs will be provided. The following examples are intended as purely illustrative of the various possible embodiments of the present inventive method without limiting in any way the scope of this invention.

TRIVALENT ANTIMONY COMPOUNDS

' The analysis for administration of drug stibophen (a trivalent antimony compound) demonstrates that although no longer used for systemic therapy of schistosomiasis, trivalent antimony compounds are valuable drugs for iontophoretic administration into the bladder-lower ureters and the colo-rectal intestine. According to the systemic therapy of schistosomasis, stibophen used to be supplied by intramuscular injection (*Rollo IM: Drugs used in the Chemotherapy of Helminthiasis, in The Pharmacological Basis of Therapeutics, Goodman L:S: and Gilman A. eds., 3'rd edition, The Macmillan Company, New York, 1058–1086, 1965) and one recommended course of therapy comprised: day 1–2 ml (Sb 17 mg); day 2–3.5 ml (Sb 28 mg); day 3–5 ml (Sb 28 mg); day 3–5 ml (Sb 42.5 mg); and six further doses of 5 ml at two day intervals. Then the course is repeated two weeks later. The end result is that maximum plateau concentrations in plasma, including those in the vesical and Inferior Mesenteric veins, will be less than 5 mcg/ml after a complete treatment regimen (two courses) of stibophen.

The method of the present invention for administering the same drug is illustrated in the following example.

EXAMPLE

Iontophoretic administration of stibophen

A catheter is inserted into the bladder, residual urine is drained and 100 ml of a stibophen solution is instilled. Electrode and power source connections are made as described above, the electrode in the catheter is of negative polarity and a constant DC current of 20–30 mA is applied for 20 minutes. The amount of drug delivered per unit time, Rt may be expressed, according Phipps et al (U.S. Pat. No. 4,744,787), as:

$$Rt\ max\ (mg/hr) = 3600\ MI/F$$

where M is the molecular weight of the drug ion (daltons), I is the intensity of current (milliamperes) and F is Faraday's constant, or expressing the time in minutes and incorporating valency (v), as:

$$Rt\ max\ (mg/min) = (6.22 \times 10^{-4}) MI/v$$

Accordingly, the quantity, R stib max, of the negatively charged moiety, antimony bis-(catechol-3,5-disulphonate), having a molecular weight of 654 daltons and a valency of 4, iontophoretically administered over 20 minutes using a current of 20–30 mA is:

$$R\ stib\ max = 40{-}60\ mg.$$

Antimony comprises 20% (w/w) of the negatively charged moiety, therefore the amount of antimony delivered is:

$$R\ sb\ max = 8{-}12\ mg.$$

Considering a transference number (tr) (expressing the fraction of total transported charge shared by a given ion) of 10–100%, the quantity of antimony administered iontophoretically into the bladder wall will fall in the approximate range of 1–10 mg. Considering a volume of the bladder tissue of 60 cm$^3$, it follows that bladder tissues, including vesical capillaries, will be exposed to antimony concentrations ranging from 17 to 170 mcg/cc, both intracellular and extracellular.

The markedly elevated tissues levels attained by localized iontophoretic administration of trivalent antimonites into the bladder tissues offers several unique advantages as:

1) the intracellular binding of these drugs within the adder wall and their slow elimination rate of 10%/day assures the release of therapeutic quantities into the bladder capillaries for at least one week;

2) the trivalent antimonites will bind to erythrocytes entering the capillaries from the arterioles;

3) viable adult schistosomes are located "downstream" in the vesical venules and veins and will ingest the antimony laden erythrocytes as well as facing exposure to the high plasma levels;

4) eggs-miracidia entrapped in the bladder tissues may be exposed to inhibitory or lethal concentrations of antimony, thereby halting the sustained release of factors provoking immune responses, with their attendant pathological damage already described;

5) the total quantity of antimony administered during a single treatment is less than the initial "sensitivity test" of 17 mg injected at the commencement of systemic therapy, so that systemic side effects (always excepting the unexpected allergic reaction) will be non-existent, 6) the peristaltic opening and closing of the ureteric mouths into the bladder permits diffusive an iontophoretic transport into the lumen and intermittent iontophoretic delivery of the antimonites into the ureteric walls.

Iontophoretic administration of trivalent antimonites into colo-rectal region is in principle very similar.

It will be appreciated that, although the above description was focussed upon specific volumes of infusion, electrical currents and times of treatment, the invention is broadly applicable to a wide range of these variables: volumes of infusion ranging from 20–500 ml, currents ranging from 2–32 mA, treatment times varying from 8–30 minutes. Also, several other trivalent antimonites are equally well suited for iontophoretic administration, as antimony sodium (or potassium) tartrate, sodium antimonyl gluconate, antimony sodium thioglicollate, antimony thioglicollamide, sodium antimony dimercaptosuccinate. The concentration of the trivalent antimonites solution can range from 0.2% to 10% and is preferably administered at a concentration of about 0.5–1%.

Pentavalent Antimony Compounds

Administration of pentavalent antimony compounds results in much higher Sb plasma (ECF) levels than does the administration of the trivalent compounds. Pentavalent antimony compounds are still in use for diseases caused by the parasite, leishmanium, but never gained a role in the treatment of schistosomiasis. The typical course of treatment with sodium stibogluconate, which is the most commonly used pentavalent antimony compound, consists of 6 sequential daily injections, each containing the equivalent of 600 mg of pentavalent antimony (*Rollo IM : Miscellaneous Drugs Used in the Treatment of Protozoal Infections; In The Pharmacological Basis of Therapeutics. Goodman L. S. and Gilman A., EDS, 3'rd edition: The Macmillan Company, New York. 1135–1143, 1965). By the sixth day, ECF-Plasma levels will asymptote to minimum and maximum values of approximately 40 mcg/ml and 80 mcg/ml over a 24 hour period.

Applying the same or similar catheterisation techniques, volumes of infusion, polarity, electrical currents and times of treatment, as described for the trivalent compounds and following the same calculation method, the amounts of antimony administered are RSb max 20 –30 mg at 20–30 mA. and with a minimum tr value of 10%, RSb is 2–3 mg respectively. Considering a bladder tissue volume of 60 cc having a ECF volume of 14 cc, the concentrations attained by antimony in bladder ECF fluid are C Sb max 1430–2140 mcg/ml, and incorporating a transference number tr of 10%, C Sb=143–214 mcg/ml.

Thus, following a single iontophoretic treatment of 20 minutes duration, both vesical-ureteric and colo-rectal ECF will contain concentrations of pentavalent Sb well in excess of those attained following a 6 day course of systemic therapy. Taking the lowest value calculated above, over a 24 hour period ECF levels will have maximum and minimum values of 143 mcg/ml and 72 mcg/ml respectively, as compared to corresponding values of 80 mcg/ml and 40 mcg/ml following a full course of systemic therapy. Since the maximum dose delivered by an iontophoretic treatment is about one twentieth the dose in a single daily injection, as with iontophoretic administration of the trivalent compounds, the question of systemic toxicity does not arise, and consequently the iontophoretic treatment can be repeated as often as is deemed clinically necessary. Niridazole, metrifonate, oxamniquine.

Niridazole, Metrifonate, Oxamniquine

In the course of this application it has been emphasized that localized iontophoretic administration of antischistosomal agents is an adjunct to, and not a replacement for, treatments with conventional systemic therapies. If these two forms of therapy are administered in the correct temporal sequence systemic administration precedes iontophoretic administration by at least 1–2 hours then, if the systemically and the iontophoretically delivered drugs are one and the same, tissue levels of the drug in the iontophoretic target areas will be higher than were the drug administered systemically alone; and if the two drugs are different agents, then the antischistosomal effects in the iontophoretic target areas will either be additive or synergistic.

For purposes of illustration, the variables of the iontophoretic technique are the same as mentioned above for the antimony compounds.

Niridazole has been virtually abandoned because, when systemically administered in therapeutic dose of 1750 mg/day for 5 days to a 70 kg person, severe toxicity frequently occurs. The quantities and derived concentrations of iontophoretically administrated niridazole (N) in bladder-ureteric and colo-rectal tissues are R N max=53–80 mg, with a tr of 10%, R N=5–8 mg, C N 0 88–132 mcg/ml.

It is noteworthy that the total dose delivered iontophoretically is about 1/100 the dose taken orally, so that systemic toxic effects are a non-issue. Because of toxic effects of systemically administered niridazole, systemic therapy prior to iontophoresis will be with one of the other oral agents.

When metrifonate (M) is iontophoretically administered, the following quantities and derivative concentrations will be found in bladder-ureteric and colo-rectal tissues: R M max=64–96 mg, with a tr of 5% R M=3.2–4.8 mg and C M=53–80 mcg/ml. The attained concentration is considerably higher than levels achieved by the preceding systemic administration should metrionate be the drug used, or if another antischistosomal drug were administered systemically, the resulting tissues levels of the two agents are either additive or synergistic within the iontophoresed regions.

When oxamniquine (0) is iontophoretically administered the quantities and derivative concentrations are R O max=72–108 mg, with a tr of 5% R 0=3.6–5.4 mg and C 0=60 –90 mcg/ml.

Corticosteroid and Antischistosomal Drugs

The present invention provides further a method of treatment of schistosomasis by localized iontophoretic administration of corticosteroid drugs in association with at least one antischistosomal drug, in order to eradicate the schistosomal infestation and at the same time to reduce tissue damage caused by eggs-miracidia trapped in bladder ureteric and colo-rectal tissues. Corticosteroids are the most reliable drugs available for the purpose of reducing inflammation caused by cell-mediated immune reactions but they have not been used for treatment of schistosomiasis. The dexamethasone sodium phosphate (Dm Na P) is the corticosteroid used for illustrative purpose.

Systemic anti-inflammatory doses of 8 mg/day of dexamethasone in 4 divided oral administrations results in clinically effective plasma (tissues) levels of 7–19 ng (nanograms)/ml (* Meikle AW, Clarke D H, Tyler F H: Cushing Syndrome From Low Doses of Dexamethasone : JAMA : 235, (15): 1592–1593, 1976). Tissues levels required for therapeutic effect are low, about 1/1000 of those supplied for other drugs discussed above and so there is far mor latitude provided for drug concentrations in the infusion, electrical currents and times of application. As an example, 100 ml of Dm Na P in a 0.01–0.05% solution instilled into the bladder and colon-rectum with currents of 4–5 mA over 5–10 minutes using an electrode of negative polarity would supply very adequate localized anti-inflammatory tissue levels. It may prove necessary to repeat iontophoretic treatment every 48–72 hours over 2–3 weeks. Even so total systemic dose administered over this period of time is too low to cause any appreciable side effects.

The same principles apply to bladder-ureteric and colorectal administration (by iontophoresis) of other esterified corticosteroid drugs such as hydrocortisone sodium hemisuccinate, prednisolone sodium phosphate, methylprednisolone sodium succinate, betamethasone sodium phosphate, with suitable currents, times of application and concentrations.

Another aspect of the present invention is related to the iontophoretic/electrophoretic administration of two different antischistosomal drugs simultaneously. The drugs are so selected that they inhibit/destroy schistosomes at two different points of their life-cycle: adult worms and eggs. The drugs are synergistic in their antischistosomal (adult worm) effects.

The presence of two different ionized drugs in the same solution greatly complicates the electrochemistry involved and the amount of each drug iontophoresed is less than if either drug were the only ionic species (plus its counterion) in solution. Petelentz has supplied an approximation pertaining to iontophoretic delivery rates of different ions in the same solution (*Petelenz T. J.: Selected Topics in Iontophoresis, PhD Thesis: The University of Utah: 45–81, 1989).

There is no analogous method for calculating electrophoretic delivery rates of different drugs, except under special circumstances (U.S. Pat. No. 4,878,892) and these must be measured experimentally. Nevertheless the phenomenon of electrophoresis will administer non ionized and even "counter" ionized drugs in appreciable quantities by means of bulk fluid flow (*Pikal M. S.: Pharm. Res. 7(3) 213–221, 1990).

Illustratively the administration of 11 combinations each of two drugs will be described. For all 11 combinations of drugs, a cathodic electrode is applied to a solution of the drugs instilled either into the bladder o into the colon-rectum. For purposes of illustration only the variables nominated are again: an infusion volume of 100 ml, an electric current of 20–30 mA and an application time of 20 minutes.

The 11 combination of drugs are hereinafter described.

I. Trivalent and Pentavalent Antimonials

A clinically appealing combination is one of a trivalent antimonite and a pentavalent antimony compound as for example, stibophen and sodium stibogluconate. Iontophorosed into bladder ureteric and colorectal tissues together, these two drugs will achieve:

1. Localized tissue levels of stibophen lethal to adult worms.
2. Localized ECF levels of sodium stibogluconate which will inhibit or destroy schistosomal eggs.

Iontophoretic treatment schedules may require adjusting for reduced rates of administration of each individual agent and also for their markedly different rates of excretion. An example of one logical clinical regimen is as follows: the infusion volume is 100 ml containing equal parts 1% stibophen and Na stibogluconate, the electric current (negative polarity) is 30 mA and is applied for 30 minutes. Treatments with both drugs are conducted on day 1 and day 2 —the "loading" dose—, Na stibogluconate is administered at 2 day intervals with stibophen added at weekly intervals. Treatments continue until fecal and urinary egg counts are reported as negative.

II Trivalent Antimonite and Niridazole

Application of current using a negative electrode results in iontophoresis of the trivalent antimonite but the positively charged niridazole is administered by electrophoresis only. As treatment proceeds, the rising pH of the solution, brought about by generation of hydroxyl ions at the negative electrode-drug solution interface, will cause decreasing ionization of niridazole and, therefore, an increasing rate of electrophoretic administration.

Trivalent antimonites interrupt the glycolytic pathway in adult worms and, judging by its side effects in humans, niridazole interferes with schistosomal transmitter substances similar to some neurotrasmitters in the human brain, thus, these 2 drugs will likely exert synergistic effects against adult worms. In addition, the anti-inflammatory properties of niridazole will reduce tissue damage caused by implanted eggs.

III Trivalent Antimonite and Metrifonate

An electric current applied by a cathodic electrode will result in iontophoresis of both the trivalent antimonite and metrifonate. Metrifonate, an organophosphate, inhibits enzymes termed acetylcholinesterases and schistosomal worms are much more sensitive to this form of enzyme inhition than are humans. This, a trivalent antimonite and metrifonate will likely exert synergistic actions against adult worms.

IV Trivalent Antimonite and Oxamniquine

The drug oxamniquine is positively charged so that treatment with this combination will result in iontophoresis of the trivalent antimonite and electrophoresis of oxamniquine. The specific sites of action of oxamniquine are uncertain but its unique selectivity (male S. mansoni worms) indicate very strongly that they are not the same as those of antimony, therefore, synergism is again likely. This same unique selectivity of oxamniquine limits this combination to colorectal instillation for treatment of S. mansoni infestations.

V Trivalent Antimonite and Praziquantel

Praziquantel is only very slightly soluble in water and it is effectively non-ionized. Nevertheless, it is probably the single most useful drug for systemic treatment of schistosomal diseases. It is effective at very low concentrations and its site of action is the schistosomal membranes. These properties recommend electrophoretic administration of praziquantel in conjunction with iontophoresis of a trivalent antimonite. Their combined actions will almost certainly be synergistic.

VI Trivalent Antimonite and Esterified Corticosteroid

Both of these groups of drugs are negatively charged so that application of an electric current under a cathodic electrode results in iontophoresis of each. Strictly speaking, corticosteroids neither inhibit nor destroy schistosomes in any of their forms, but the reduction of inflammatory damage induced by implanted eggs is a valuable adjunct to the destruction of adult worms by the trivalent antimonite.

VII Pentavalent Antimony Compound and Niridazole

Iontophoresis of a pentavalent antimonial combined with electrophoresis of niridazole will exert a synchronous chemotherapeutic effect against both eggs and adults worms, with the added benefit of niridazoles anti-inflammatory side effect.

VIII Pentavalent Antimony Compound and Metrifonate

Iontophoresis of both these negatively charged drugs will exert therapeutic effects against adult worms and eggs.

IX Pentavalent Antimony Compound and Oxamniquine

Using a cathodic electrode, iontophoresis of the pentavalent antimonial will be accompanied by electrophoresis of the positively charged oxamniquine. The resultant chemotherapeutic effects are directed against S. mansoni adult worms and against the eggs of all schistosomal species.

X Pentavalent Antimony Compound and Praziquantel

The combination of a pentavalent antimonial and praziquantel is particularly useful because of the former's action against eggs & praziquantels proven effectiveness against adult worms of all major pathogenic species.

XI Pentavalent Antimony Compound and an Esterified Corticosteroid

With a cathodic electrode, both of these drugs are iontophoresed into overlying tissues, the pentavalent antimonial will inhibit/destroy eggs, whether 'rapped in tissues or moving into urine and feces, and the corticosteroid will reduce the inflammatory reactions associated with entrapped eggs. This particular combination highlights importance of preceding or concurrent systemic chemotherapy: in the presence of heavy infestation, it is pointless to direct chemotherapeutic effort solely against the eggs and leave numerous adult worms free to lay more.

Still another aspect of the present invention is related to the administration of a solution of at least a certain antischistosomal drug with any physiological buffer/electrolyte.

For electrophoretic administration into bladder-ureteric and colo-rectal tissues, a certain quota of ions in solution (approximately >0.5% or 5 mg/ml) is required to efficiently carry these currents for the times specified. Failure to supply this minimum concentration will result in recruitment of additional ionic species and reduce transference number for the drugs. In absence of additional "contaminating" ions in the drug solutions, recruitment takes place through hydrolysis of water (U.S. Pat. No. 4,744,787). Even if it is recognized that additional ionic species will lower the theoretical delivery rates for drugs contained in the same solution, the addition of certain electrolytes will be less detrimental than accumulation of $H^+$ or $OH^-$ in a pure drug solution.

One good example, although by no means the only one, are the phosphate buffers, either sodium or potassium hydrogen and dihydrogen phosphates.

In addition, mixed buffers permit free choice of polarity and provide an effective means of inducing electrophoretic transport of drugs.

The admixture of buffering agents with specified anti-schistosomal drugs for the purpose of iontophoretic/electrophoretic administration into the bladder-ureteric or colo-rectal tissues is of particular clinical merit because, when effectuated at adequate concentrations of about 0.3-1.0%, will reduce the chances of acid-alkali burning of tissues almost to zero.

That is claimed is:

1. A method of treating schistosomal infestations by both adult worms and eggs-miracidia, localized in the veins, venules and nearby tissues either of the bladder and ureters or of the colo-rectal regions of the intestine which comprises the steps of:
    a) inserting a catheter via the urethra into the bladder or via rectum within a selected segment of the colo-rectal region, said catheter encompassing an active electrode of appropriate polarity connected to an external power source;
    b) infusing via said catheter at least an antischistosomal drug in the form of a solution;
    c) placing in contact with a suitable skin location, an indifferent electrode of opposite polarity to said active electrode;
    d) supplying an electrical current from said external power source with matching polarities to said active electrode and said indifferent electrode thereby permitting passage of current and consequent administration by iontophoresis of said at least an antischistosomal drug into the tissues surrounding the active electrode.

2. A method according to claim 1, wherein said at least an antischistosomal drug is an ionizable compound.

3. A method according to claim 1, wherein said antischistosomal drug is difficulty ionizable and is administered in conjunction with at least another ionizable drug.

4. A method according to claim 1, comprising administering two antischistosomal drugs.

5. A method according to claim 1, comprising administering an antischistosomal drug in conjunction with an anti-inflammatory drug.

6. A method according to claim 1, wherein said antischistosomal drug is selected from the group consisting of a trivalent antimony compound, a pentavalent antimony compound, niridazole, metrifonate, oxamniquine, praziquantel, mixture thereof and salts thereof.

7. A method according to claim 1, wherein said antischistosomal drug is a trivalent antimony compound selected from salts of trivalent antimony with organic acids.

8. A method according to claim 1, wherein said antischistosomal drug is a pentavalent antimony compound selected from salts of pentavalent antimony with organic acids.

9. A method according to claim 1, wherein said antischistosomal drug is niridazole.

10. A method according to claim 1, wherein said antischistosomal drug is metrifonate.

11. A method according to claim 1, wherein said antischistosomal drug is oxamniquine.

12. A method according to claim 1, wherein said antischistosomal drug is praziquantel.

13. A method according to claim 4, wherein said two drugs are a trivalent and a pentavalent antimony compounds.

14. A method according to claim 4, wherein said two drugs are either one of a trivalent or pentavalent antimony compound, and metrifonate.

15. A method according to claim 4, wherein said two drugs are either one of a trivalent or pentavalent antimony compound, and niridazole.

16. A method according to claim 4, wherein said two drugs are either one of a trivalent or pentavalent antimony compound, and oxamniquine.

17. A method according to claim 4, wherein said two drugs are either one of a trivalent or pentavalent antimony compound.

18. A method according to claim 5, wherein said anti-inflammatory drug is an ionized esterified corticosteroid compound.

19. A method according to claim 5, wherein said anti-inflammatory drug is a corticosteroid compound consisting of dexamethasone phosphate.

20. A method according to claim 1, wherein said antischistosomal drug is contained in said solution at a concentration ranging from 0.2 to 10% w/v.

21. A method according to claim 1, comprising administering from 20 to 500 ml of said solution containing said at least one antischistosomal drug.

* * * * *